United States Patent [19]
Clancy et al.

[11] Patent Number: 6,110,494
[45] Date of Patent: *Aug. 29, 2000

[54] CISAPRIDE MINI-TABLET FORMULATIONS

[75] Inventors: Maurice Joseph Anthony Clancy, Athlone; Kenneth Iain Cumming, Dublin, both of Ireland

[73] Assignee: Elan Corporation, plc, Dublin, Ireland

[ * ] Notice: This patent issued on a continued prosecution application filed under 37 CFR 1.53(d), and is subject to the twenty year patent term provisions of 35 U.S.C. 154(a)(2).

[21] Appl. No.: 08/995,583

[22] Filed: Dec. 22, 1997

Related U.S. Application Data
[60] Provisional application No. 60/035,027, Jan. 13, 1997.

[30] Foreign Application Priority Data

Jan. 3, 1997 [IE] Ireland ..................................... 970001

[51] Int. Cl.⁷ ................................. A61K 9/62; A61K 9/50
[52] U.S. Cl. .......................... 424/461; 424/489; 424/490; 424/493; 424/494; 424/451; 424/457; 424/458; 424/459
[58] Field of Search ..................................... 424/451, 456, 424/457, 458, 462, 461, 484, 486, 487, 488, 490, 493, 494, 497

[56] References Cited

U.S. PATENT DOCUMENTS

| | | | |
|---|---|---|---|
| 4,205,073 | 5/1980 | Sherlock et al. | 424/266 |
| 4,259,314 | 3/1981 | Lowey et al. | 424/19 |
| 4,369,172 | 1/1983 | Schor et al. | 424/19 |
| 4,606,909 | 8/1986 | Bechgaard et al. | 424/21 |
| 4,609,909 | 9/1986 | Bechgaard et al. | |
| 4,704,285 | 11/1987 | Alderman | 424/468 |
| 4,874,613 | 10/1989 | Hsiao | 424/458 |
| 4,904,479 | 2/1990 | Illum | 424/490 |
| 4,973,469 | 11/1990 | Mulligan et al. | 424/461 |
| 4,983,401 | 1/1991 | Eichel et al. | |
| 5,015,479 | 5/1991 | Mulligan et al. | 424/457 |
| 5,026,559 | 6/1991 | Eichel et al. | 424/458 |
| 5,102,668 | 4/1992 | Eichel et al. | 424/490 |
| 5,128,142 | 7/1992 | Mulligan et al. | 424/457 |

(List continued on next page.)

FOREIGN PATENT DOCUMENTS

| | | | |
|---|---|---|---|
| 0 076 530 | 4/1983 | European Pat. Off. | C07D 211/58 |
| 0 177 000 A1 | 4/1986 | European Pat. Off. | A61K 9/52 |
| 0 325 086 A2 | 7/1989 | European Pat. Off. | A61K 9/22 |
| 0 645 136 A2 | 3/1995 | European Pat. Off. | A61K 9/22 |
| 0 803 251 | 10/1997 | European Pat. Off. | A61K 31/00 |
| 89/06957 | 8/1989 | WIPO | A61K 9/22 |
| 94/05262 | 3/1994 | WIPO | A61K 9/16 |
| 94/06416 | 3/1994 | WIPO | A61K 9/24 |
| 96/14070 | 5/1996 | WIPO | A61K 31/445 |
| 96/26718 | 9/1996 | WIPO | A61K 9/22 |
| 97/02017 | 1/1997 | WIPO | A61K 9/14 |
| 97/20562 | 6/1997 | WIPO | A61K 31/445 |

OTHER PUBLICATIONS

*Drug Development and Industrial Pharmacy*, vol. 18, No. 16, 1992, pp. 1719–1739; Hawley, A.R., et al.: "Physical and Chemical Characterization of Thermosoftened Bases for Molten Filled Hard Gelatin Capsule Formulations".

*Primary Examiner*—Thurman K. Page
*Assistant Examiner*—Brian K. Seidleck
*Attorney, Agent, or Firm*—Marla J. Church

[57] ABSTRACT

A sustained release cisapride oral dosage formulation suitable for once-daily administration comprises a plurality of mini-tablets containing cisapride or a salt thereof with an organic acid and capable of releasing cisapride at different sites along the gastrointestinal tract. The mini-tablets include a proportion of immediate release tablets and a proportion of tablets which release cisapride in response to the pH environment at a given site in the distal regions of the gastrointestinal tract and which include cisapride or a salt thereof embedded in a matrix of hydrophilic polymer, said matrix being coated with a pH dependent polymer, the formulation having a Cmax/Cmin ratio under steady state conditions of 2:1 or less as evidenced by a substantially flat plasma profile in vivo.

9 Claims, 4 Drawing Sheets

U.S. PATENT DOCUMENTS

| | | | |
|---|---|---|---|
| 5,133,974 | 7/1992 | Paradissis et al. | 424/480 |
| 5,238,686 | 8/1993 | Eichel et al. | 424/461 |
| 5,260,069 | 11/1993 | Chen | 424/451 |
| 5,326,570 | 7/1994 | Rudnic et al. | 424/458 |
| 5,422,123 | 6/1995 | Conte et al. | 424/479 |
| 5,447,729 | 9/1995 | Belenduik et al. | 424/490 |
| 5,464,633 | 11/1995 | Conte et al. | 424/480 |
| 5,472,710 | 12/1995 | Klokkers-Bethke et al. | 424/468 |
| 5,495,024 | 2/1996 | Itoh et al. | 548/267.8 |
| 5,500,227 | 3/1996 | Oshlack et al. | 424/476 |
| 5,501,863 | 3/1996 | Rossling et al. | 424/489 |
| 5,508,040 | 4/1996 | Chen | 424/451 |
| 5,558,879 | 9/1996 | Chen et al. | 424/480 |
| 5,624,683 | 4/1997 | Andoh et al. | 424/470 |
| B1 4,389,393 | 10/1985 | Schor et al. | 424/19 |

CISAPRIDE MINI-TABLET FORMULATIONS

This application claims the benefit of U.S. Provisional Application Ser. No. 60/035,027, filed Jan. 13, 1997, abandoned.

FIELD OF THE INVENTION

This invention relates to a controlled release cisapride formulation for oral administration.

BACKGROUND OF THE INVENTION

Cisapride is a stimulant of gastrointestinal motility which is used for the symptomatic relief of gastroesophageal reflux disease (GORD) and thus is effective as a gastroprokinetic agent. Cisapride is the subject of EP 0 076 530B.

Cisapride is poorly soluble and thus may be administered as a salt, such as the tartrate salt, for oral administration or, alternatively, formulated in a way which increases solubility of the base in an aqueous environment as found in the gastrointestinal tract.

WO 96/14070 concerns extended release formulations comprising cisapride-(L)-tartrate embedded in viscous hydrophilic polymers which release cisapride in a racemic form comprising equal amounts of the diastereomeric salt forms (+)-cisapride-(L) tartrate and (−)-cisapride-(L) tartrate which have equal dissolution rates. The hydrophilic polymers swell in contact with an aqueous environment creating a porous matrix from which the cisapride is gradually released.

Cisapride is currently administered in the form of immediate release tablets containing cisapride as the monohydrate equivalent to 10 mg or 20 mg of cisapride. The dosage regimen (at least initially) is 10 mg four times a day. Furthermore, the drug must be administered 15 min. before meals.

There is a need for a controlled release formulation of cisapride containing 40 mg of cisapride that can be administered once-daily and which is bioequivalent in terms of AUC (area under the curve) to the current standard treatment (10 mg q.i.d.) allowing for direct substitution of the standard treatment.

Furthermore, the release rate of cisapride from the formulation should be such that it delivers a smooth plasma concentration versus time profile with minimal peak to trough variation. The effect of food on the absorption profile should be minimised as should the potential for 'dose dumping'. A formulation having all of these features would enhance patient acceptability as well as the safety and tolerability of the formulation relative to the standard treatment.

SUMMARY OF THE INVENTION

The invention provides a controlled release cisapride oral dosage formulation suitable for once-daily administration, said formulation comprising a plurality of mini-tablets containing cisapride or a salt thereof with an organic acid and capable of releasing cisapride at different sites along the gastrointestinal tract, said mini-tablets including a proportion of immediate release tablets and a proportion of tablets which release cisapride in response to the pH environment at a given site in the distal regions of the gastrointestinal tract and which include cisapride or a salt thereof embedded in a matrix of hydrophilic polymer, said matrix being coated with a pH dependent polymer, the formulation having a Cmax/Cmin ratio under steady state conditions of 2:1 or less.

The solubility of cisapride is pH dependent. The higher the pH the lower the solubility. The consequence of this is that the solubility of the drug and hence the dissolution of a formulation containing cisapride will decrease in the more distal regions of the gastrointestinal tract resulting in a significant decrease in absorption in these regions.

The formulation according to the invention overcomes these problems by ensuring a continuous release of cisapride or a salt thereof throughout the gastrointestinal tract.

Cisapride has a relatively short half life. Thus, in order to allow for successful once-daily dosing a controlled release mechanism has to be incorporated into the dosage form. The formulation according to the invention has such a controlled release mechanism and achieves bioequivalence with the cisapride 10 mg q.i.d. dosage regimen as hereinafter demonstrated.

Cisapride can be used in the form of cisapride base but preferably a salt with an organic acid is used. Any suitable pharmaceutically acceptable organic acid can be used which interacts with the other components of the formulation to achieve a formulation with a Cmax/Cmin ratio under steady state conditions of 2:1 or less as evidenced by a substantially flat plasma profile in vivo.

Preferably, the mini-tablets which release cisapride in the distal regions of the gastrointestinal tract include a proportion of mini-tablets which release cisapride at a pH in the range 5.5–6.5 and a proportion of mini-tablets which release cisapride at a pH in the range 6.5–7.5.

Further, preferably, the immediate release mini-tablets, the pH 5.5–6.5 responsive mini-tablets and the pH 6.5–7.5 responsive mini-tablets are present in a ratio of 2:3:4.

An especially suitable salt of cisapride for use in accordance with the invention is cisapride tartrate due to its superior water solubility properties relative to the cisapride base. A particularly suitable tartrate salt is cisapride-(L)-tartrate.

The cisapride base or salt thereof is embedded in a hydrophilic matrix polymer or mixture thereof to form cores from which there is a sustained release of cisapride. Preferred such hydrophilic polymers include a mixture of a hydroxypropyl methylcellulose and a hydroxypropyl cellulose.

A suitable hydroxypropyl methylcellulose is one sold under the Trade Mark Methocel, especially Methocel K100 M.

A suitable hydroxypropyl cellulose is one sold under the Trade Mark Klucel, especially Klucel LF.

Further, suitably the hydroxypropyl methylcellulose and the hydroxypropyl cellulose are used in a ratio of approximately 2:1.

The immediate release tablets consist of cisapride or a salt thereof as hereinbefore defined together with typical tabletting agents such as: a disintegrant of the type sold under the Trade Mark Explotab; a diluent or compacting agent such as microcrystalline cellulose, more especially microcrystalline cellulose sold under the Trade Mark Avicel, for example Avicel pH101; a lubricant such as magnesium stearate; and a glidant such as colloidal silicon dioxide sold under the Trade Mark Aerosil, for example Aerosil 200.

The mini-tablets which release cisapride in a controlled manner in the distal regions of the gastrointestinal tract have a core of cisapride or a salt thereof embedded in a hydrophilic polymer or mixture thereof of the type described above coated with a pH dependent polymer to form pH responsive mini-tablets.

pH responsive mini-tablets as used herein which release cisapride at a pH in the range 5.5–6.5 or 6.5–7.5 are preferably coated with a polymer which is soluble in that pH range or, alternatively, is permeable to cisapride and water in the particular range so as to bring about the required release of cisapride from the mini-tablets at the relevant pH.

The term soluble polymer as used herein is used collectively to include polymers which are water soluble and polymers which are permeable to cisapride and water in the indicated pH range.

Suitable polymers which are freely permeable to a poorly soluble active ingredient such as cisapride in the indicated pH ranges are polymers sold under the Trade Mark Eudragit and which comprise copolymers of methacrylic acid and methacrylic acid esters.

A suitable polymer for controlled release of cisapride or a salt thereof in the pH range 5.5–6.5 from a pH responsive mini-tablet according to the invention is Eudragit L.

A suitable polymer for controlled release of cisapride or a salt thereof in the pH range 6.5–7.5 from a pH responsive mini-tablet according to the invention is Eudragit S.

Alternatively, the skilled person can use other enteric polymers known in the art, such as cellulose acetate phthalate, cellulose acetate trimellitate, hydroxypropyl methylcellulose phthalate, hydroxypropyl methylcellulose acetate succinate, shellac, carboxymethylethylcellulose or polyvinylacetate phthalate (sold under the Trade Marks Opadry Aqueous Enteric and Opadry Enteric).

The sustained release cores of the pH responsive mini-tablets are coated in conventional manner with the desired pH dependent polymer so as to form said pH responsive mini-tablets. The coating solution/suspension will suitably contain the polymer together with a plasticizer such as diethyl phthalate, an anti-tacking agent such as talc and a solvent or mixture of solvents such as an organic solvent or a mixture of an organic solvent and water.

The coating can be carried out in a conventional coating pan or in an automatic coating system such as an Accela Cota 48 (Accela Cota 48 is a Trade Mark).

Suitably the mini-tablets in accordance with the invention are loaded in the desired ratio into a capsule or sachet for oral administration. Preferably, the mini-tablets are loaded into capsules which can be formed of soft or hard gelatin.

The formulation according to the invention preferably has a minimal food effect as measured by a change in Cmax when administered with food.

It is necessary to avoid excessive plasma levels of cisapride because these may give rise to cardiovascular complications. These complications have been experienced by certain patients taking the standard q.i.d. formulation. Accordingly, there is a need to avoid the potential for dose dumping with cisapride formulations. Food is found to have an enhancing effect on the absorption of cisapride.

The formulation according to the invention is not disrupted or damaged by the presence of food nor is the release mechanism altered as hereinafter demonstrated. Rather, the formulation according to the invention has a smooth plasma profile with minimal fluctuations in plasma levels. The F ratio for Cmax (fasted versus fed) for Example 2 is 1.01, showing that there is no impact of food on Cmax with this formulation.

DETAILED DESCRIPTION OF THE INVENTION

The invention will be further illustrated by the following Examples.

In the Examples all ingredients used were USP/EP standard with the exception of cisapride/cisapride tartrate which was obtained from Janssen Pharmaceutica N.V., Beerse, Belgium.

EXAMPLE 1

(Comparative)

A. Immediate release (IR) cisapride tartrate.

IR cisapride tartrate mini-tablets were formed from the following ingredients in the indicated amounts by blending to form a blend of 22 kg:

| Ingredient | % |
|---|---|
| Cisapride tartrate | 16.8 |
| Explotab | 10.0 |
| Avicel pH 101 | 71.2 |
| Aerosil 200 | 1.0 |
| Magnesium stearate | 1.0 |

The ingredients, with the exception of the magnesium stearate, were blended for 45 min. The magnesium stearate was then added and blending continued for 5 min. The blend was then tabletted in a Horn-Noack tabletting machine to the following specifications:

Punch design: 3.8 mm round deep concave

No. of punches: 27

Cam size: 6 mm

Target hardness: 50 N

Target fill weight: 35.48 mg

Press speed: 70,000 tablets/hour

Compression force setting: 1.80 mm

Pre pressure setting: 6.00 mm

The tablets disintegrated in under 1 min.

B. Eudragit L coated IR mini-tablets.

The IR mini-tablets prepared as described in Section A were coated with a coating suspension having the following composition:

| Material | % |
|---|---|
| Eudragit L 12.5 | 49.87 |
| Talc | 2.47 |
| Diethyl phthalate | 1.27 |
| Isopropyl alcohol | 43.33 |
| Purified water | 3.07 |

The suspension batch size was 15 kg. The coating equipment and conditions were as follows:

Coating equipment: Accela Cota 10"
Inlet temperature: 40.1° C.
Outlet temperature: 32.0–33.4° C.
Air pressure: 1.3 bar
Mean spray rate: ca. 45 g/min
Coating level: 15.07%, % weight gain –300 g sample removed at 12.5% weight gain.
12540 g coating solution applied equivalent 1251 g coating solids =13.90% theoretical weight gain vis à vis 15.07% actual weight gain
The coated tablet batch size was 9 kg.
The 12.5% weight gain coated IR tablets were selected for preparation of the formulations used in the studies described in Examples 4–6 below.
The coated tablets had the following disintegration:
Disintegration:
Tablets intact after 1 hour in pH 1.2;
Tablets disintegrated after 30 minutes in pH 6.8

C. Eudragit S coated IR mini-tablets.

The IR mini-tablets prepared as described in Section A were coated with a coating suspension having the following composition:

| Material | % |
| --- | --- |
| Eudragit S 12.5 | 49.86 |
| Talc | 2.46 |
| Diethyl phthalate | 1.26 |
| Isopropyl alcohol | 43.33 |
| Purified water | 3.06 |

The suspension batch size was 16 kg. The coating equipment and conditions were as follows:

Coating equipment: Accela Cota 10"
Inlet temperature: 32.4–43.0° C.
Outlet temperature: 29.4–35.6° C.
Air pressure: 1.3 bar
Mean spray rate: 40 g/min
Coating level: 14.36% weight gain –300 g sample removed at 8% weight gain.
12290 g coating solution applied equivalent to 1223 g coating solids=13.59% theoretical weight gain vis à vis 14.36% actual weight gain
The coated tablet batch size was 9 kg
The 8% weight gain coated IR tablets were selected for preparation of the formulations used in the studies described in Examples 4–6 below.
The coated tablets had the following disintegration:
Disintegration:
Tablets intact after 1 hour in pH 1.2;
Tablets disintegrated after 1 hour in pH 6.8

D.

The mini-tablets prepared as described in Sections A, B and C and selected for use in the studies of Examples 4–6 below were loaded into hard gelatin capsules in the ratio 1:4:4, respectively.

EXAMPLE 2

A. Immediate release (IR) cisapride tartrate.

Immediate release mini-tablets were prepared as described in Example 1, Section A.

B. Cisapride tartrate sustained release (SR) mini-tablets

Cisapride tartrate SR mini-tablets were formed from the following materials and in the indicated amounts to form a blend size of 10 kg.

| Material | % |
| --- | --- |
| Cisapride tartrate | 16.8 |
| Methocel K100M | 20.0 |
| Klucel LF | 10.0 |
| Avicel pH 101 | 51.2 |
| Aerosil 200 | 1.0 |
| Magnesium stearate | 1.0 |

The materials, with the exception of the magnesium stearate, were blended for 45 min. The magnesium stearate was then added and the blending continued for 7 min. The blend was then tabletted in a Horn-Noack tabletting machine according to the specifications given below. If any sticking occurred on tabletting then the blend was reblended for a further 7 min., optionally following the addition of further 0.5% of magnesium stearate.

Punch design: 3.8 mm round deep concave
No. of punches: 27
Cam size: 6 mm
Target hardness: 50 N
Target fill weight: 34.64 mg
Press speed: 70,000 tablets/hour
Compression force setting: 1.80 mm
Pre pressure setting: 5.1 mm
The dissolution of the mini-tablets thus prepared in 0.1N HCl, using Paddles at 50 r.p.m. was as follows:

| Time (hrs) | % released |
| --- | --- |
| 0.5 | 20.48 |
| 1.0 | 29.64 |
| 2.0 | 42.09 |
| 3.0 | 51.40 |
| 4.0 | 60.55 |

C. Eudragit L coated SR mini-tablets.

The SR mini-tablets prepared as described in Section B were coated with a coating suspension having the following composition:

| Material | % |
| --- | --- |
| Eudragit L 12.5 | 66.45 |
| Talc | 3.25 |
| Diethyl phthalate | 1.65 |
| Isopropyl alcohol | 25.0 |
| Purified water | 4.05 |

The suspension batch size was 2 kg. The coating equipment and conditions were as follows:

Coating equipment: Hi Cota (Hi Cota is a Trade Mark)
Inlet temperature: 60–82° C.
Outlet temperature: 30–32° C.
Air pressure: 1 bar
Spray rate: 4 g/min Coating level: 20.85% weight gain The coated batch size was 690 g.

D. Eudragit S coated SR mini-tablets.

The SR mini-tablets prepared as described in Section B were coated with a coating suspension having the following composition:

| Material | % |
|---|---|
| Eudragit S 12.5 | 49.90 |
| Talc | 2.45 |
| Diethyl phthalate | 1.27 |
| Isopropyl alcohol | 43.3 |
| Purified water | 3.05 |

The suspension batch size was 2 kg. The coating equipment and conditions were as follows:

Coating equipment: Hi Cota

Inlet temperature: 50–75° C.

Outlet temperature: 30–32° C.

Air pressure: 1 kg cm$^{-2}$

Spray rate: 3g/min

Coating level: 9.98% weight gain

The coated batch size was 630 g.

E. mini-tablets prepared in Sections A, C and D and selected for use in s of Examples 4–6 below were loaded into hard gelatin capsules in the ratio 2:3:4, respectively.

EXAMPLE 3

Example 2B was repeated but varying the amount of Methocel and magnesium stearate used as well as the blending time in order to optimise the sustained release core. The experimental design was 4×2$^2$ factorial-12 runs-2.5 kg batches. The levels of Methocel and magnesium stearate and post-magnesium stearate blending times shown in Table 1 produced satisfactory mini-tablets.

TABLE 1

| Run No. | Methocel Content | Magnesium Stearate | Post Magnesium Stearate Blend Time |
|---|---|---|---|
| 1 | 12% | 1.25% | 5 min. |
| 2 | 12% | 1.50% | 5 min. |
| 3 | 20% | 1.25% | 10 min. |
| 4 | 16% | 1.25% | min. |
| 5 | 16% | 1.50% | 10 min. |
| 6 | 12% | 1.25% | 10 min. |
| 7 | 20% | 1.50% | 5 min. |
| 8 | 16% | 1.25% | 10 min. |
| 9 | 20% | 1.25% | 5 min. |
| 10 | 20% | 1.50% | 10 min. |
| 11 | 12% | 1.50% | 10 min. |
| 12 | 16% | 1.50% | 5 min. |

EXAMPLE 4

The in vitro dissolution of the encapsulated products prepared in Example 1, Section D (40 mg) and Example 2, Section E (40 mg) was determined. A summary of the dissolution conditions is shown in Table 2.

TABLE 2

| Conditions | Encapsulated |
|---|---|
| Medium | pH 6.8 citrate/phosphate + 0.5% SLS |
| Apparatus | Paddles |
| Rotation speed (rpm) | 50 |
| Detection | HPLC |
| Wavelength (nm) | 220 |
| Temperature (° C.) | 37.0 |
| Volume (ml) | 900 |

SLS (sodium lauryl sulphate) was required to solubilise cisapride at pH 6.8.

Figure 1:
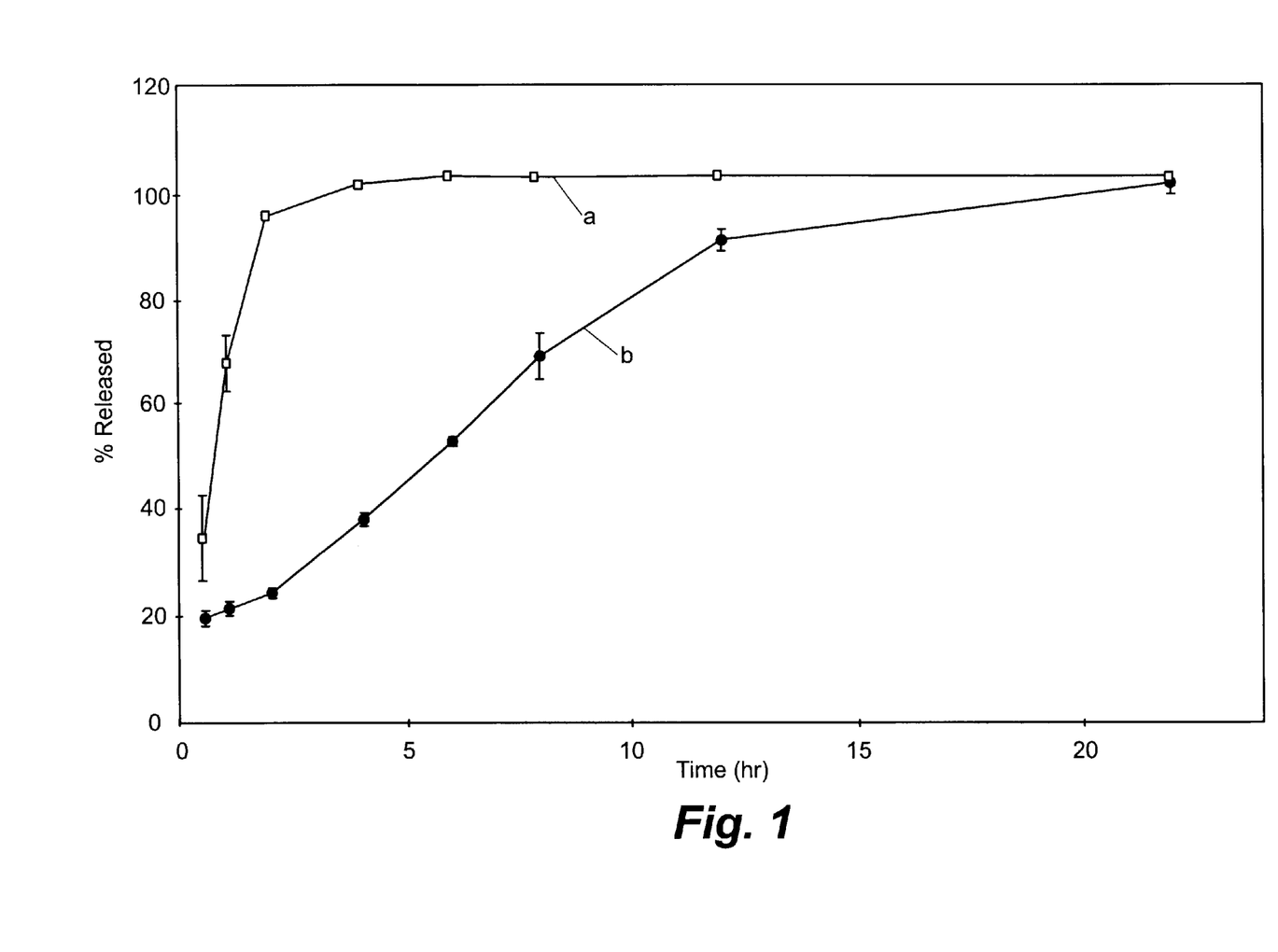
FIG. 1 is a graph of in vitro dissolution (% release) versus time (hours) for blends of mini-tablets prepared in Examples 1 and 2.

The results are shown in FIG. 1, wherein curve a) corresponds to the product of Example 1 and curve b) corresponds to the product of Example 2. It will be noted that curve b) is substantially sustained meeting the criteria for an effective once-daily cisapride formulation.

EXAMPLE 5

A fasted/fed study with twenty volunteers and a 5 leg crossover was carried out on the encapsulated products prepared in Example 1, Section D (40 mg) and Example 2, Section E (40 mg) and also a reference, namely the current q.i.d. formulation sold under the Trade Mark Prepulsid by Janssen Pharmaceutica NV. The results are shown in Table 3 and FIG. 2

Figure 2:
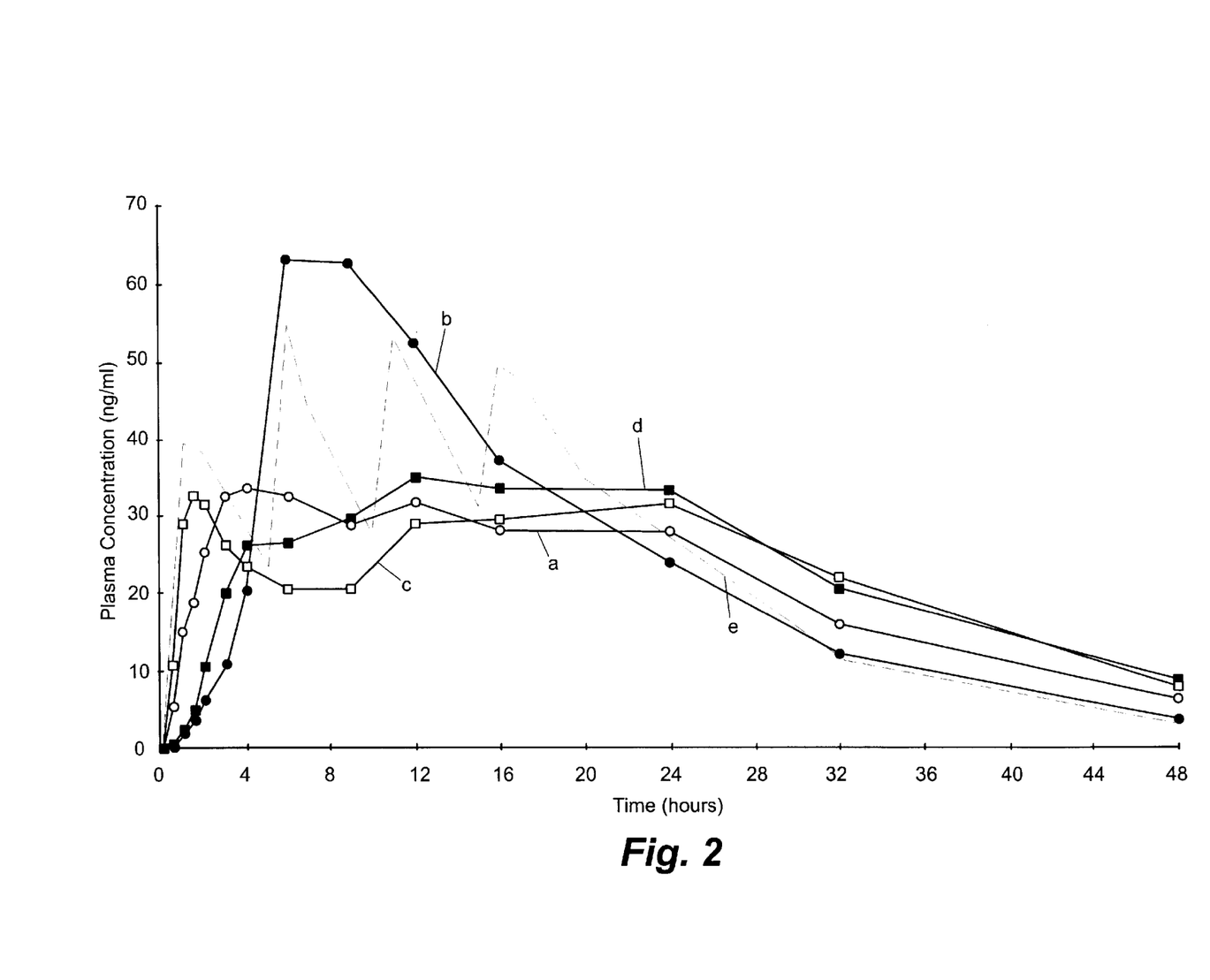
FIG. 2 is a graph of plasma concentration (ng/ml) versus time (hours) for blends of mini-tablets prepared in Examples 1 and 2 (fasted and fed) relative to a reference.

In FIG. 2 curve a) corresponds to the product of Example 1 when administered under fasted conditions; curve b) corresponds to the product of Example 1 when administered under fed conditions; curve c) corresponds to the product of Example 2 when administered under fasted conditions; curve d) corresponds to the product of Example 2 when administered under fed conditions; and curve e) corresponds to the reference.

It will be observed that the product of Example 2 showed no noticeable food effect, namely the Cmax level was comparable under fasted and fed conditions. The product of Example 1 on the other hand showed almost a doubling of Cmax during the fed state.

Also the profile for the product of Example 2 is very flat with a very low peak to trough ratio over the time period 2–24 hours.

TABLE 3

| | Cisapride: Statistical Analysis | | | | |
|---|---|---|---|---|---|
| Parameter | Example 1 Fasted | Example 1 Fed | Example 2 Fasted | Example 2 Fed | Reference |
| $C_{max}$ | 39.61 ± 9.45 | 74.43 ± 19.25 | 38.32 ± 10.20 | 38.62 ± 11.90 | 58.50 ± 13.51 |
| $T_{max}$ | 9.65 ± 6.69 | 7.42 ± 1.84 | 12.24 ± 10.26 | 14.65 ± 5.52 | 1.10 ± 0.31 |
| AUC (0–48 h) | 1051.35 ± 277.14 | 1184.71 ± 325.32 | 1107.12 ± 355.38 | 1149.46 ± 342.70 | 1182.02 ± 331.81 |
| AUC (infinity) | 1243.08 ± 362.23 | 1216.95 ± 338.47 | 1410.69 ± 599.05 | 1411.93 ± 560.16 | 1240.68 ± 360.25 |
| F ratio (infinity) ($AUC_{Test}/AUC_{Reference}$) | 1.03 ± 0.25 | 1.00 ± 0.25 | 1.13 ± 0.38 | 1.15 ± 0.35 | — |

EXAMPLE 6

A steady state biostudy was carried out comparing the products of Examples 1 and 2 and the reference (Prepulsid). The results are shown in Table 4.

TABLE 4

| Parameter | Example 1 | Example 2 | Reference |
|---|---|---|---|
| $Cmax_{ss}$ | 91.82 ± 18.64 | 62.01 ± 10.81 | 71.73 ± 12.77 |
| $Tmax_{ss}$ | 5.17 ± 2.62 | 1.53 ± 0.70 | 1.08 ± 0.35 |
| $AUC_{0-24ss}$ | 1230.17 ± 258.15 | 998.91 ± 218.72 | 1160.68 ± 268.46 |
| $Fss_{(0-24\ hours)}$ ($AUC_{Test}/AUC_{Reference}$) | 1.07 ± 0.09 | 0.88 ± 0.16 | — |

The data show that Example 2 is bioequivalent to the reference Prepulsid at steady state as well as following single dose.

EXAMPLE 7

(Comparative)

'In a further biostudy the reference product Prepulsid was compared with a number of multiparticulate dosage forms, namely sustained release beads or pellets. It was found that the bioavailability of the beads was very low when compared with the reference.

A study with products consisting i) solely of beads and ii) beads and IR mini-tablets prepared as in the case of Example 1, Section A in a ratio of 8:1 was carried out. The respective products were loaded into hard gelatin capsules (size 00).

The sustained release beads were formed from the following materials in the indicated amounts:

| Material | mg/capsule |
|---|---|
| Cisapride tartrate | 52.92 |
| Kollidon 30 (Kollidon is a Trade Mark) | 5.30 |
| Talc | 20.21 |
| Non-pareil seeds (1–2 mm) | 65.91 |
| Ethocel 7 cps (Ethocel is a Trade Mark) | 0.89 |
| Isopropyl alcohol | N/A |
| Aerosil 200 | 1.35 |
| Hard gelatin capsule (Size 0) | 97.46 |

The isopropyl alcohol was not present in the final product but used for the application and timing solutions.

Figure 3:
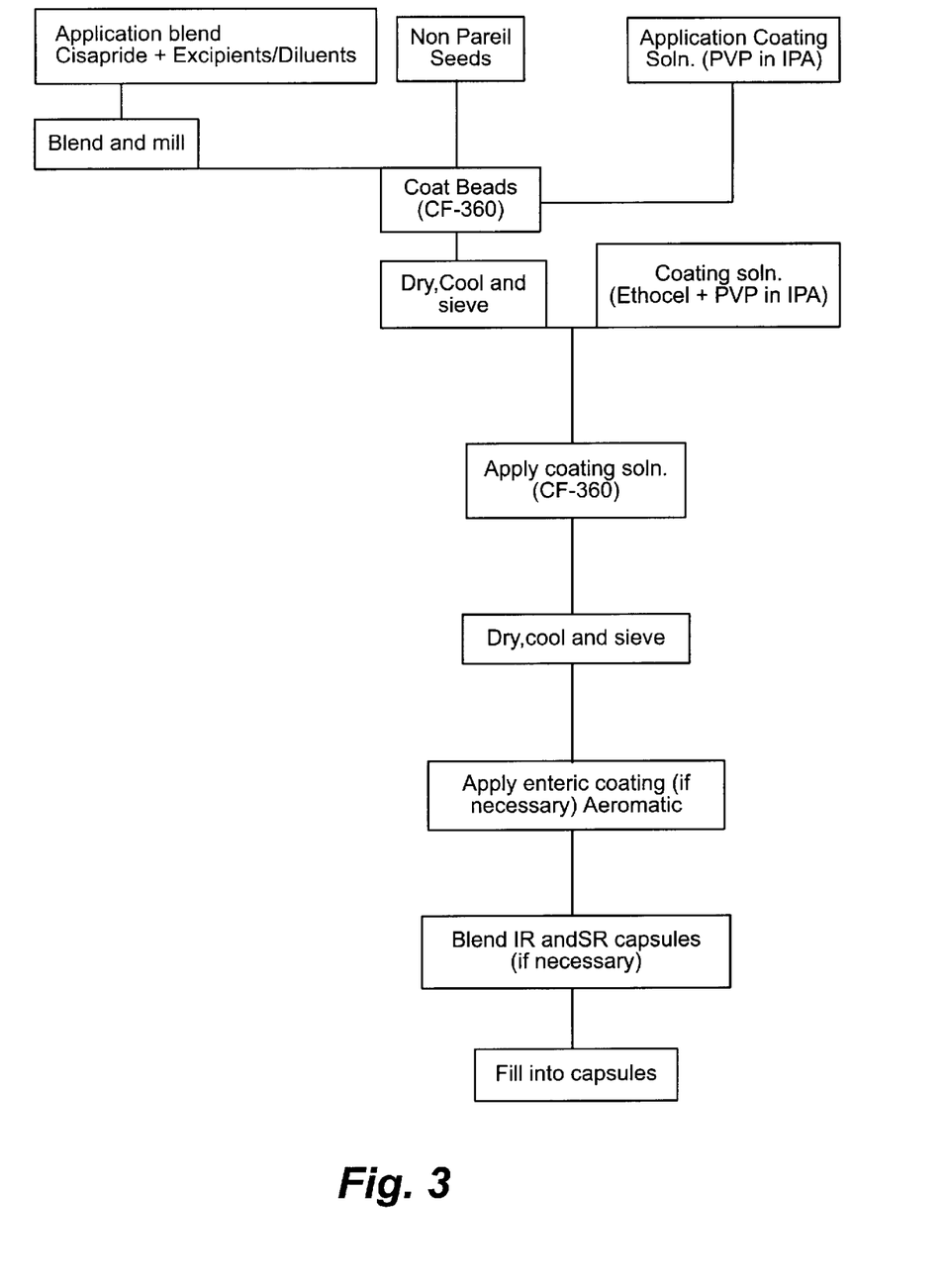
FIG. 3 is a process flow chart outlining the steps used in preparing the multiparticulate formulation of Example 7.

A process flow chart outlining the steps taken in preparing the two products for use in the biostudy is set forth in FIG. 3.

As indicated above, preparation i) was a size 00 opaque white gelatin capsule containing sustained release beads equivalent to 40 mg cisapride. The sustained release beads were coated to a level of 5.25% corresponding to product e) in Table 5.

TABLE 5

| | Time (hours) | | | | | | | | | |
|---|---|---|---|---|---|---|---|---|---|---|
| Product | 0.17 | 0.33 | 0.5 | 1 | 2 | 4 | 5 | 8 | 12 | 16 |
| Uncoated | 73.00 | 78.94 | 80.74 | 83.09 | 86.46 | 90.92 | 94.24 | 96.59 | 100.35 | 101.41 |
| a — 4.25% | 24.52 | 37.88 | 46.54 | 60.49 | 74.86 | 89.01 | 95.47 | 98.61 | 101.14 | 102.09 |
| b — 4.5% | 20.43 | 30.35 | 36.89 | 48.14 | 60.70 | 75.45 | 83.70 | 88.62 | 94.31 | 97.48 |
| c — 4.75% | 16.84 | 25.14 | 30.70 | 40.80 | 53.30 | 68.44 | 77.86 | 83.87 | 91.26 | 96.38 |
| d — 5% | 10.02 | 15.34 | 18.84 | 26.00 | 34.55 | 46.46 | 55.12 | 61.54 | 70.10 | 75.92 |
| e — 5.25% | 9.28 | 14.79 | 18.51 | 25.46 | 34.86 | 48.39 | 57.97 | 65.28 | 75.58 | 82.72 |

Table 5 includes dissolution data for uncoated beads (a) as well as beads coated to levels of 4.25% (b), 4.5% (c), 4.75% (d), 5.0% (e) and 5.25% (f). All of these coating levels were found to give the desired in vitro release profiles. The results are also depicted in FIG. 4.

Figure 4:
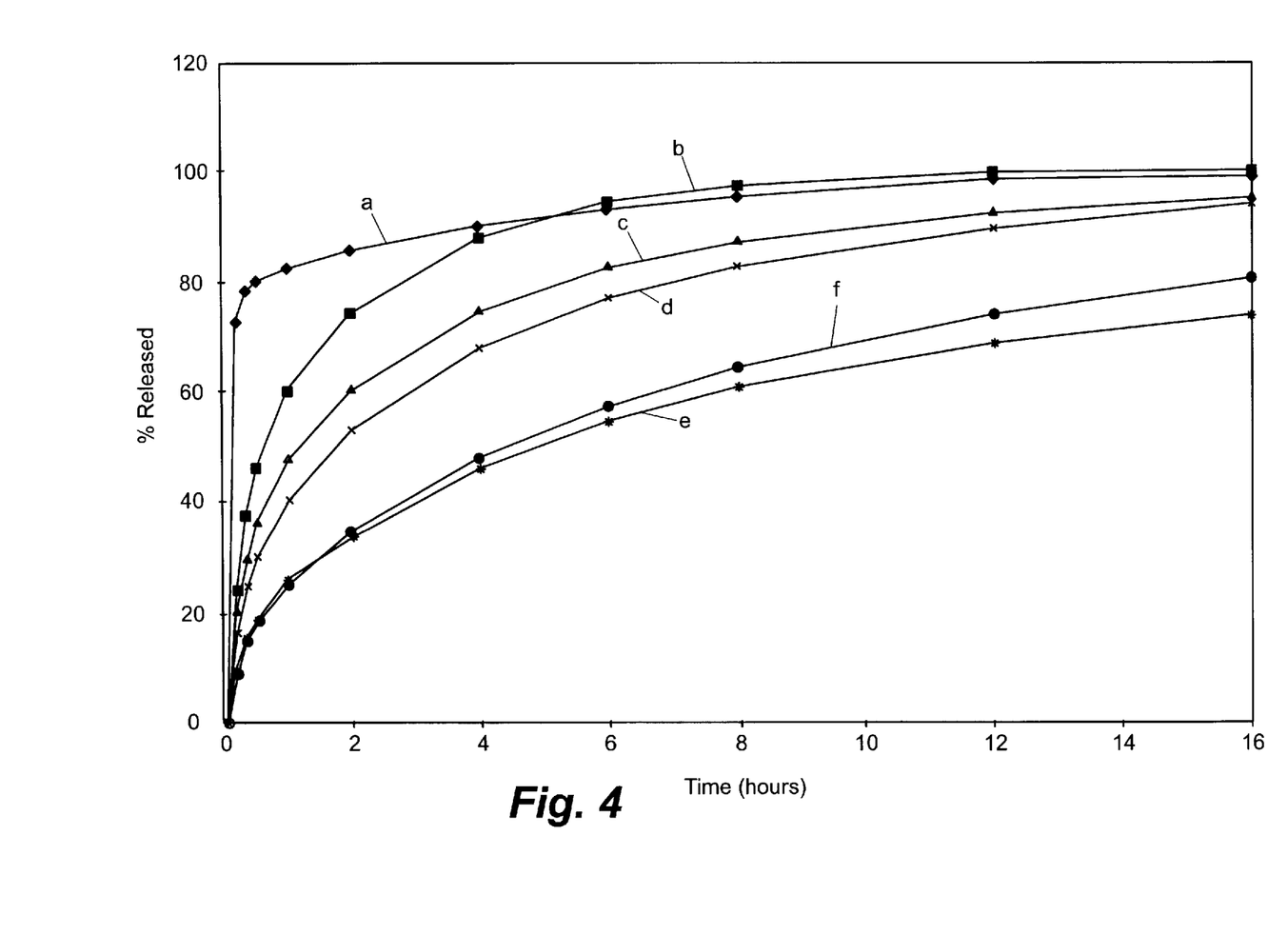
FIG. 4 is a graph of in vitro dissolution (% release) versus time (hours) for the formulations described in Example 7.

In FIG. 4: curve a) corresponds to uncoated beads; curve b) corresponds to beads coated to a level of 4.25%; curve c) corresponds to beads coated to a level of 4.5%; curve d) corresponds to beads coated to a level of 4.75%; curve e) corresponds to beads coated to a level of 5.0% and curve f) corresponds to beads coated to a level of 5.25%.

Preparation ii) consisted of an immediate release mini-tablet as prepared in Example 1, Section A and enteric coated sustained release beads equivalent to 40 mg cispride. The IR mini-tablets were equivalent to 4.44 mg cisapride and the enteric coated SR beads were equivalent to 35.56 mg cisapride. The enteric coated beads were SR beads coated to 4.75% with rate controlling polymer (formulation c, Table 5) and then further coated with approximately 5% of Eudragit L.

As indicated above, the bioavailability of each of formulations i) and ii) was very low, with an F value relative to the reference (Prepulsid) in the region 0.1–0.3. This biostudy indicates that beaded/pellet formulations are not suitable dosage forms for the once-daily administration of cisapride.

What is claimed is:

1. A controlled release cisapride oral dosage formulation suitable for once-daily administration, said formulation comprising a plurality of mini-tablets containing cisapride or a salt thereof with an organic acid and capable of releasing cisapride at different sites along the gastrointestinal tract, said mini-tablets including a proportion of immediate release tablets and a proportion of tablets which release cisapride in response to the pH environment at a given site in the distal regions of the gastrointestinal tract and which include a sustained release matrix of cisapride or a salt thereof and hydrophilic polymer, said matrix being coated with a pH dependent polymer, the formulation having a $C_{max}/C_{min}$ ratio under steady state conditions of 2:1 or less wherein the mini-tablets which release cisapride in the distal regions of the gastrointestinal tract include a proportion of mini-tablets which release cisapride at a pH in the range 5.5–6.5 and a proportion of mini-tablets which release cisapride at a pH in the range 6.5–7.5.

2. A formulation according to claim 1, wherein the immediate release mini-tablets, the pH 5.5–6.5 responsive mini-tablets and the pH 6.5–7.5 responsive mini-tablets are present in a ratio of 2:3:4, respectively.

3. A formulation according to claim 1, wherein the cisapride is in the form of cisapride-(L)-tartrate.

4. A formulation according to claim 1, wherein the hydrophilic polymers of the matrix are selected from a mixture of a hydroxypropyl methylcellulose and a hydroxypropyl cellulose.

5. A formulation according to claim 1, wherein the pH dependent polymer is a co-polymer of methacrylic acid and methacrylic acid esters.

6. A formulation according to claim 1, wherein the mini-tablets are contained in a capsule or sachet.

7. A formulation according to claim 1 which has a minimal food effect as measured by a change in $C_{max}$ when administered with food.

8. A controlled release cisapride oral dosage formulation suitable for once daily administration, comprising a plurality of mini-tablets containing cisapride or a pharmaceutically acceptable salt thereof with an organic acid, a portion of said mini-tablets capable of immediate release of cisapride and a portion capable of controlled release of cisapride, said controlled release mini-tablets each comprising a controlled release matrix of said cisapride or pharmaceutically acceptable salt thereof and a hydrophilic polymer, and a coating over said matrix of a pH dependent polymer, and wherein a first portion of said controlled release mini-tablets includes a said pH dependent polymer for controlled release of an effective amount of cisapride at a pH in the range of 5.5–6.5, and a second portion of said controlled release mini-tablets includes a said pH dependent polymer for controlled release of an effective amount of cisapride at a pH in the range of 6.5–7.5.

9. A controlled release cisapride oral dosage formulation as claimed in claim 8, wherein said controlled release mini tablets include at least a third portion having a pH dependent polymer for controlled release of cisapride at a third pH different from said first and second pH's.

* * * * *